(12) United States Patent
Emanuel

(10) Patent No.: US 9,226,650 B2
(45) Date of Patent: *Jan. 5, 2016

(54) SURGICAL CUTTING DEVICE AND METHOD FOR ITS USE

(71) Applicant: Smith & Nephew, Inc., Memphis, TN (US)

(72) Inventor: Mark Hans Emanuel, Bioemendaal (NL)

(73) Assignee: Smith & Nephew, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/744,611

(22) Filed: Jun. 19, 2015

(65) Prior Publication Data

US 2015/0282698 A1    Oct. 8, 2015

Related U.S. Application Data

(60) Continuation of application No. 14/081,801, filed on Nov. 15, 2013, now Pat. No. 9,089,358, which is a continuation of application No. 11/929,940, filed on Oct. 30, 2007, which is a division of application No. 11/780,759, filed on Jul. 20, 2007, now Pat. No. 8,061,359, which is a continuation of application No. 09/486,977, filed as application No. PCT/NL98/00504 on Sep. 4, 1998, now Pat. No. 7,249,602.

(30) Foreign Application Priority Data

Sep. 4, 1997    (NL) ..................................... 1006944

(51) Int. Cl.
*A61B 1/00* (2006.01)
*A61B 1/12* (2006.01)
*A61B 19/00* (2006.01)
*A61B 17/32* (2006.01)
*A61B 17/42* (2006.01)

(52) U.S. Cl.
CPC .............. *A61B 1/12* (2013.01); *A61B 17/32002* (2013.01); *A61B 17/320016* (2013.01); *A61B 19/5212* (2013.01); *A61B 2017/4216* (2013.01); *A61B 2217/005* (2013.01); *A61B 2217/007* (2013.01)

(58) Field of Classification Search
USPC ............. 600/104–105, 118, 153–159; 606/46
See application file for complete search history.

(56) References Cited

U.S. PATENT DOCUMENTS 1,585,934 A    5/1926 Muir
1,666,332 A    4/1928 Hirsch
(Continued)

FOREIGN PATENT DOCUMENTS

DE    3339322 A1    5/1984
DE    3206381 C2    7/1986
(Continued)

OTHER PUBLICATIONS

ACMI Corporation, "Dolphin II Hysteroscopic Fluid Management Systems," ACMI Corporation, 2002 (1 page).
(Continued)

*Primary Examiner* — Matthew J Kasztejna
(74) *Attorney, Agent, or Firm* — Nixon Peabody LLP

(57) ABSTRACT

A surgical endoscopic cutting device includes cutting elements fitted in a protective tube. The device has an inlet for fluid, a discharge outlet for tissue and fluid, and a further outlet that discharges most of the fluid.

19 Claims, 3 Drawing Sheets

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender |
| 3,791,379 A | 2/1974 | Storz |
| 3,812,855 A | 5/1974 | Banko |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman |
| 4,146,405 A | 3/1979 | Timmer |
| 4,198,958 A | 4/1980 | Utsugi |
| 4,203,444 A | 5/1980 | Bonnell |
| 4,210,146 A | 7/1980 | Banko |
| 4,246,902 A | 1/1981 | Martinez |
| 4,247,180 A | 1/1981 | Norris |
| 4,258,721 A | 3/1981 | Parent |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt |
| 4,493,698 A | 1/1985 | Wang |
| 4,517,977 A | 5/1985 | Frost |
| 4,543,965 A | 10/1985 | Pack |
| 4,567,880 A | 2/1986 | Goodman |
| 4,589,414 A | 5/1986 | Yoshida |
| 4,601,290 A | 7/1986 | Effron |
| 4,606,330 A | 8/1986 | Bonnet |
| 4,630,598 A | 12/1986 | Bonnet |
| 4,644,952 A | 2/1987 | Patipa |
| 4,649,919 A | 3/1987 | Thimsen |
| 4,700,694 A | 10/1987 | Shishido |
| 4,706,656 A | 11/1987 | Kuboto |
| 4,718,291 A | 1/1988 | Wood |
| 4,737,142 A | 4/1988 | Heckele |
| 4,749,376 A | 6/1988 | Kensey |
| 4,756,309 A | 7/1988 | Sachse |
| 4,819,635 A | 4/1989 | Shapiro |
| 4,844,064 A | 7/1989 | Thimsen |
| 4,850,354 A | 7/1989 | McGurk-Burleson |
| 4,856,919 A | 8/1989 | Takeuchi |
| 4,867,157 A | 9/1989 | McGurk-Burleson |
| 4,924,851 A | 5/1990 | Ognier |
| 4,940,061 A | 7/1990 | Terwilliger |
| 4,950,278 A | 8/1990 | Sachse |
| 4,955,882 A | 9/1990 | Hakky |
| 4,986,827 A | 1/1991 | Akkas |
| 4,998,527 A | 3/1991 | Meyer |
| 4,998,914 A | 3/1991 | Wiest |
| 5,007,917 A | 4/1991 | Evans |
| 5,027,792 A | 7/1991 | Meyer |
| 5,037,386 A | 8/1991 | Marcus |
| 5,105,800 A | 4/1992 | Takahashi |
| 5,106,364 A | 4/1992 | Hayafuji |
| 5,112,299 A | 5/1992 | Pascaloff |
| 5,116,868 A | 5/1992 | Chen |
| 5,125,910 A | 6/1992 | Freitas |
| 5,133,713 A | 7/1992 | Huang |
| 5,152,744 A | 10/1992 | Krause |
| 5,158,553 A | 10/1992 | Berry |
| 5,163,433 A | 11/1992 | Kagawa |
| 5,169,397 A | 12/1992 | Sakashita |
| 5,176,677 A | 1/1993 | Wuchinich |
| 5,195,541 A | 3/1993 | Obenchain |
| 5,226,910 A | 7/1993 | Kajiyama |
| 5,244,459 A | 9/1993 | Hill |
| 5,254,117 A | 10/1993 | Rigby |
| 5,269,785 A | 12/1993 | Bonutti |
| 5,270,622 A | 12/1993 | Krause |
| 5,275,609 A | 1/1994 | Pingleton |
| 5,288,290 A | 2/1994 | Brody |
| 5,304,118 A | 4/1994 | Trese |
| 5,312,399 A | 5/1994 | Hakky |
| 5,312,425 A | 5/1994 | Evans |
| 5,312,430 A | 5/1994 | Rosenbluth |
| 5,320,091 A | 6/1994 | Grossi |
| 5,347,992 A | 9/1994 | Pearlman |
| 5,350,390 A | 9/1994 | Sher |
| 5,364,395 A | 11/1994 | West, Jr. |
| 5,374,253 A | 12/1994 | Burns, Sr. |
| 5,390,585 A | 2/1995 | Ryuh |
| 5,392,765 A | 2/1995 | Muller |
| 5,395,313 A | 3/1995 | Naves |
| 5,403,276 A | 4/1995 | Schechter |
| 5,409,013 A | 4/1995 | Clement |
| 5,411,513 A | 5/1995 | Ireland |
| 5,425,376 A | 6/1995 | Banys |
| 5,429,601 A | 7/1995 | Conley |
| 5,443,476 A | 8/1995 | Shapiro |
| 5,449,356 A | 9/1995 | Walbrink |
| 5,456,689 A | 10/1995 | Kresch |
| 5,490,819 A | 2/1996 | Nicholas |
| 5,490,860 A | 2/1996 | Middle |
| 5,492,537 A | 2/1996 | Vancaillie |
| 5,498,258 A | 3/1996 | Hakky |
| 5,527,331 A | 6/1996 | Kresch |
| 5,549,541 A | 8/1996 | Muller |
| 5,556,378 A | 9/1996 | Storz |
| 5,563,481 A | 10/1996 | Krause |
| 5,569,164 A | 10/1996 | Lurz |
| 5,569,254 A | 10/1996 | Carlson |
| 5,569,284 A | 10/1996 | Young |
| 5,591,187 A | 1/1997 | Dekel |
| 5,601,583 A | 2/1997 | Donahue |
| 5,601,603 A | 2/1997 | Illi |
| 5,602,449 A | 2/1997 | Krause |
| 5,603,332 A | 2/1997 | O'Connor |
| 5,630,798 A | 5/1997 | Beiser |
| 5,649,547 A | 7/1997 | Ritchart |
| 5,669,927 A | 9/1997 | Boebel |
| 5,672,945 A | 9/1997 | Krause |
| 5,674,179 A | 10/1997 | Bonnet |
| 5,676,497 A | 10/1997 | Kim |
| 5,695,448 A | 12/1997 | Kimura |
| 5,702,420 A | 12/1997 | Sterling |
| 5,709,698 A | 1/1998 | Adams |
| 5,730,752 A | 3/1998 | Alden |
| 5,733,298 A | 3/1998 | Berman |
| 5,741,286 A | 4/1998 | Recuset |
| 5,741,287 A | 4/1998 | Alden |
| 5,749,885 A | 5/1998 | Sjostrom |
| 5,749,889 A | 5/1998 | Bacich |
| 5,759,185 A | 6/1998 | Grinberg |
| 5,772,634 A | 6/1998 | Atkinson |
| 5,775,333 A | 7/1998 | Burbank |
| 5,782,849 A | 7/1998 | Miller |
| 5,807,240 A | 9/1998 | Muller |
| 5,807,282 A | 9/1998 | Fowler |
| 5,810,770 A | 9/1998 | Chin |
| 5,810,861 A | 9/1998 | Gaber |
| 5,814,009 A | 9/1998 | Wheatman |
| 5,833,643 A | 11/1998 | Ross |
| 5,840,060 A | 11/1998 | Beiser |
| 5,857,995 A | 1/1999 | Thomas |
| 5,873,886 A | 2/1999 | Larsen |
| 5,899,915 A | 5/1999 | Saadat |
| 5,911,699 A | 6/1999 | Anis |
| 5,911,722 A | 6/1999 | Adler |
| 5,913,867 A | 6/1999 | Dion |
| 5,916,229 A | 6/1999 | Evans |
| 5,925,055 A | 7/1999 | Adrian |
| 5,928,163 A | 7/1999 | Roberts |
| 5,944,668 A | 8/1999 | Vancaillie |
| 5,947,990 A | 9/1999 | Smith |
| 5,951,490 A | 9/1999 | Fowler |
| 5,956,130 A | 9/1999 | Vancaillie |
| 5,957,832 A | 9/1999 | Taylor |

(56) References Cited

U.S. PATENT DOCUMENTS

| | | |
|---|---|---|
| 6,001,116 A | 12/1999 | Heisler |
| 6,004,320 A | 12/1999 | Casscells |
| 6,007,513 A | 12/1999 | Anis |
| 6,024,751 A | 2/2000 | Lovato |
| 6,032,673 A | 3/2000 | Savage |
| 6,039,748 A | 3/2000 | Savage |
| 6,042,552 A | 3/2000 | Cornier |
| 6,068,641 A | 5/2000 | Varsseveld |
| 6,086,542 A | 7/2000 | Glowa |
| 6,090,123 A | 7/2000 | Culp |
| 6,113,594 A | 9/2000 | Savage |
| 6,119,973 A | 9/2000 | Galloway |
| 6,120,147 A | 9/2000 | Vijfvinkel |
| 6,120,462 A | 9/2000 | Hibner |
| 6,132,448 A | 10/2000 | Perez |
| 6,149,633 A | 11/2000 | Maaskamp |
| 6,156,049 A | 12/2000 | Lovato |
| 6,159,160 A | 12/2000 | Hsei |
| 6,159,209 A | 12/2000 | Hakky |
| 6,203,518 B1 | 3/2001 | Anis |
| 6,217,543 B1 | 4/2001 | Anis |
| 6,224,603 B1 | 5/2001 | Marino |
| 6,244,228 B1 | 6/2001 | Kuhn |
| 6,258,111 B1 | 7/2001 | Ross |
| 6,277,096 B1 | 8/2001 | Cortella |
| 6,315,714 B1 | 11/2001 | Akiba |
| 6,358,200 B1 | 3/2002 | Grossi |
| 6,358,263 B2 | 3/2002 | Mark |
| 6,359,200 B1 | 3/2002 | Day |
| 6,402,701 B1 | 6/2002 | Kaplan |
| 6,428,486 B2 | 8/2002 | Ritchart |
| 6,494,892 B1 | 12/2002 | Ireland |
| 6,585,708 B1 | 7/2003 | Maaskamp |
| 6,610,066 B2 | 8/2003 | Dinger |
| 6,626,827 B1 | 9/2003 | Felix |
| 6,632,182 B1 | 10/2003 | Treat |
| 6,656,132 B1 | 12/2003 | Ouchi |
| 6,712,773 B1 | 3/2004 | Viola |
| 6,837,847 B2 | 1/2005 | Ewers |
| 7,025,732 B2 | 4/2006 | Thompson |
| 7,150,713 B2 | 12/2006 | Shener |
| 7,226,459 B2 | 6/2007 | Cesarini |
| 7,249,602 B1 | 7/2007 | Emanuel |
| 7,510,563 B2 | 3/2009 | Cesarini |
| 7,763,033 B2 | 7/2010 | Gruber |
| 7,922,737 B1 | 4/2011 | Cesarini |
| 8,061,359 B2 | 11/2011 | Emanuel |
| 2001/0039963 A1 | 11/2001 | Spear |
| 2001/0047183 A1 | 11/2001 | Privitera |
| 2002/0058859 A1 | 5/2002 | Brommersma |
| 2003/0050603 A1 | 3/2003 | Todd |
| 2003/0050638 A1 | 3/2003 | Yachia |
| 2003/0078609 A1 | 4/2003 | Finlay |
| 2003/0114875 A1 | 6/2003 | Sjostrom |
| 2004/0204671 A1 | 10/2004 | Stubbs |
| 2005/0043690 A1 | 2/2005 | Todd |
| 2005/0085692 A1 | 4/2005 | Kiehn |
| 2006/0036132 A1 | 2/2006 | Renner |
| 2006/0047185 A1 | 3/2006 | Shener |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams |
| 2008/0097469 A1 | 4/2008 | Gruber |
| 2008/0097470 A1 | 4/2008 | Gruber |
| 2008/0097471 A1 | 4/2008 | Adams |
| 2008/0135053 A1 | 6/2008 | Gruber |
| 2008/0146872 A1 | 6/2008 | Gruber |
| 2008/0146873 A1 | 6/2008 | Adams |
| 2008/0245371 A1 | 10/2008 | Gruber |
| 2008/0249366 A1 | 10/2008 | Gruber |
| 2008/0249534 A1 | 10/2008 | Gruber |
| 2008/0249553 A1 | 10/2008 | Gruber |
| 2008/0262308 A1 | 10/2008 | Prestezog |
| 2009/0270812 A1 | 10/2009 | Litscher |
| 2009/0270895 A1 | 10/2009 | Churchill |
| 2009/0270896 A1 | 10/2009 | Sullivan |
| 2009/0270897 A1 | 10/2009 | Adams |
| 2009/0270898 A1 | 10/2009 | Chin |
| 2010/0087798 A1 | 4/2010 | Adams |
| 2010/0152647 A1 | 6/2010 | Shener |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 4440035 A1 | 5/1996 |
| DE | 19633124 A1 | 5/1997 |
| DE | 102006022827 A1 | 12/2006 |
| EP | 0310285 A2 | 4/1989 |
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 5/1997 |
| EP | 1681022 A1 | 7/2006 |
| GB | 2093353 A | 9/1982 |
| GB | 2311468 A | 10/1997 |
| JP | 01-75416 | 5/1989 |
| JP | 2002529185 A | 9/2002 |
| JP | 2003245247 A | 9/2003 |
| NL | 1006944 C2 | 3/1999 |
| WO | WO 81/01648 A1 | 6/1981 |
| WO | WO 92/11816 A2 | 7/1992 |
| WO | WO 93/07821 A1 | 4/1993 |
| WO | WO 93/15664 A1 | 8/1993 |
| WO | WO 94/26181 A1 | 11/1994 |
| WO | WO 95/05777 A1 | 3/1995 |
| WO | WO 95/10981 A1 | 4/1995 |
| WO | WO 95/10982 A1 | 4/1995 |
| WO | WO 95/22935 A1 | 8/1995 |
| WO | WO 95/30377 A1 | 11/1995 |
| WO | WO 96/11638 A1 | 4/1996 |
| WO | WO 96/26676 A1 | 9/1996 |
| WO | WO 97/09922 A1 | 3/1997 |
| WO | WO 97/17027 A1 | 5/1997 |
| WO | WO 97/19642 A1 | 6/1997 |
| WO | WO 97/24071 A1 | 7/1997 |
| WO | WO 97/34534 A1 | 9/1997 |
| WO | WO 97/35522 A1 | 10/1997 |
| WO | WO 98/09569 A1 | 3/1998 |
| WO | WO 98/10707 A1 | 3/1998 |
| WO | WO 98/46147 A1 | 10/1998 |
| WO | WO 99/03407 A1 | 1/1999 |
| WO | WO 99/03409 A1 | 1/1999 |
| WO | WO 99/07295 A1 | 2/1999 |
| WO | WO 99/11184 A1 | 3/1999 |
| WO | WO 99/39648 A1 | 8/1999 |
| WO | WO 99/44506 A1 | 9/1999 |
| WO | WO 99/60935 A1 | 12/1999 |
| WO | WO 00/12010 A1 | 3/2000 |
| WO | WO 00/28890 A1 | 5/2000 |
| WO | WO 00/33743 A1 | 6/2000 |
| WO | WO 00/44295 A1 | 8/2000 |
| WO | WO 00/47116 A1 | 8/2000 |
| WO | WO 00/57797 A1 | 10/2000 |
| WO | WO 01/35831 A1 | 5/2001 |
| WO | WO 01/58368 A1 | 8/2001 |
| WO | WO 01/95810 A2 | 12/2001 |
| WO | WO 02/069808 A2 | 9/2002 |
| WO | WO 03/022164 A1 | 3/2003 |
| WO | WO 03/077767 A1 | 9/2003 |
| WO | WO 2005/060842 A1 | 7/2005 |
| WO | WO 2005/096963 A2 | 10/2005 |
| WO | WO 2006/105283 A2 | 10/2006 |
| WO | WO 2006/121968 A2 | 11/2006 |
| WO | WO 2006/121970 A2 | 11/2006 |

(56) References Cited

FOREIGN PATENT DOCUMENTS

| WO | WO 2007/044833 A2 | 4/2007 |
|---|---|---|
| WO | WO 2012/044705 A1 | 4/2012 |

OTHER PUBLICATIONS

ACMI Corporation, "DOLPHIN II and DISTEN-U-FLO Fluid Management Systems for Hysteroscopy", ACMI Corporation, 2002 (1 page).
Bacsko "Uterine Surgery by Operative Hysteroscopy", European Journal of Obstetrics & Gynecology and Reproductive Biology, vol. 71, pp. 219-222, 1997 (4 pages).
Haggish et al., "Diagnostic and Operative Hysterectomy," Mosby, pp. 97-105, 123-125, 127-132, 353-355, and 394-398, 1999 (27 pages).
C.R. Bard, Inc, "The HydroFlex HD System" (1 page).
Cravello et al., "Hysteroscopic Resection of Fibroids: Results with a 6-Year Follow-up Period", Journal of Gynecologic Surgery, vol. 15, No. 1, 1-5 1999 (5 pages).
Defendant Hologic Inc.'s Preliminary, Non-Binding List of Asserted Prior Art References, dated Feb. 8, 2012, in *Smith & Nephew, Inc.* v. *Hologic, Inc.*, Civil Action Nos. 11-12064-RWZ and 10-10951-RWZ, U.S. District Court for the District of Massachusetts (7 pages).
Dictionary definition of reciprocate, Merrian-Webster Dictionary, on-line edition, retrieved Mar. 20, 2013 (1 page).
Dictionary definition of rotate, Merriam-Webster Dictionary, on-line edition, retrieved Mar. 20, 2013 (1 page).
Dictionary definition of translate, Merriam-Webster Dictionary, on-line edition, retrieved Mar. 20, 2013 (1 page).
Drews et al., "Surgical Approach to Myomas: Laparoscopy and Hysteroscopy", Seminars in Reproductive Endocrinology, vol. 10, No. 4, pp. 367-377, 1992 (11 pages).
Dumesic et al., "A New Approach to Hysteroscopic Cannulation of the Fallopian Tube", Journal of Gynecologic Surgery, vol. 7, No. 1, pp. 7-9, 1991 (3 pages).
Emanuel et al., "Long-term Results of Hysteroscopic Myomectomy for Abnormal Uterine Bleeding", Obstetrics & Gynecoogy, vol. 93, No. 5, Part I, pp. 743-748, 1999 (6 pages).
European Patent Application No. 05 786 521.4-2305, Examination Report dated Apr. 21, 2010 (4 pages).
European Patent Application No. 05 786 521.4-2305, Examination Report dated Sep. 26, 2012 (5 pages).
European Patent Application No. 11 770 261.3-1657, Examination Report dated Feb. 11, 2014 (4 pages).
Exhibit P To Hologic's Opposition to Smith & Nephew's Motion for Preliminary Injunction, Redacted, filed Dec. 30, 2011, in *Smith & Nephew, Inc.* v. *Hologic, Inc.*, Civil Action No. 11-12064-RWZ, U.S. District Court for the District of Massachusetts (99 pages).
Franchini et al., "Endometrial resection: a diagnostic tool in postmenopausal women", Gynecological Endoscopy, 8, pp. 111-114, 1999 (5 pages).
"From Distention to Deficit Monitoring Taking the All-In-One Approach", W.O.M. World of Medicine (1 page).
Gerber et al., "The Endoscapel: A new endoscopic instrument for supracervical hysterectomy and morcellation of masses; clinical evaluation", European Journal of Obstetrics & Gynecology and Reproductive Biology, 86, p. S12, 1999 (1 page).
Gynecare "Motor Drive Unit" Instructions for Use (3 pages).
Gynecare X-Tract, "Tissue Morcellator", Instructions for Use (3 pages).
Gynecare, "Fluid Management System" Instructions for Use (26 pages).
Gynescope Corporation "Laser Fiber Director", Advertisement, Journal of Gynecologic Surgery, vol. 6, No. 1, 1990 (2 pages).
Hess et al., "Textbook of Bilio-Pancreatic Disease", vol. III, PICCIN, e.g. Fig 6.5.1, pp. 1584-1586, 1997 (5 pages).
Hologic's Opposition to Smith & Nephew's Motion for Preliminary Injunction, Redacted, filed Dec. 30, 2011, in *Smith & Nephew, Inc.* v. *Hologic, Inc.*, Civil Action No. 11-12064-RWZ, U.S. District Court for the District of Massachusetts (26 pages).
"HysteRo-Purator 1143-1 Technical Data" WISAP (2 pages).

International Application No. PCT/US2005/029807, International Preliminary Report on Patentability dated Feb. 28, 2007 (9 pages).
International Application No. PCT/US2005/029807, International Search Report mailed on Jun. 13, 2006 (5 pages).
International Application No. PCT/US2011/053753, International Preliminary Report on Patentability dated Apr. 2, 2013 (7 pages).
International Application No. PCT/US2011/053753, International Search Report mailed on Dec. 20, 2011 (4 pages).
Japanese Patent Application No. 2007-530014, Translation of Office Action dated Feb. 15, 2011 (10 pages).
Karl Storz "Pilot a Course to Successful Outcomes", Intermetro Industries Corporation, 2001 (2 pages).
Karl Storz "Uterine Resectoscopes for Endometrial Ablation and Resection", Advertisement, Journal of Gynecologic Surgery, vol. 6, No. 1, 1990 (3 pages).
Karl Storz, Advertisement, Journal of Gynecologic Surgery, vol. 5, No. 4, 1989 (3 pages).
Lin et al. "Clinical Applications of a New Fujinon Operating Fiberoptic Hysteroscope", Journal of Gynecologic Surgery, vol. 6, No. 2, pp. 81-87, 1990 (7 pages).
Mettler et al., "Pelviscopic uterine surgery" Surgical Endoscopy, 6, pp. 23-31, 1992 (9 pages).
Neis et al., "Hysteroscopy: Textbook and Atlas", Thieme Medical Publishers, pp. 91-103, 1994 (13 pages).
Nisolle et al., "Endometrial ablation with the Nd-YAG laser in dysfunctional bleeding" Minimally Invasive Therapy, vol. 1, pp. 35-39, 1991 (5 pages).
Olympus Product Catalogue: Part No. A2461—OP Nephroscope, Sep. 1991 (3 pages).
Park et al., "Endoscopic Management of Uterine Myoma", Yonsei Medical Journal, vol. 40, No. 6, pp. 583-588, 1999 (6 pages).
Reexamination No. 95/001,933, Action Closing Prosecution mailed Sep. 19, 2013 (41 pages).
Reexamination No. 95/001,933, Appendices 14-28 to Request for Inter Partes Reexamination of U.S. Pat. No. 7,226,459, Claim Charts for Various Claims in view of Various References (436 pages).
Reexamination No. 95/001,933, Appendix 2 to Request for Inter Partes Reexamination of U.S. Pat. No. 7,226,459, Memorandum of Decision dated Apr. 21, 2011, in *Smith & Nephew, Inc.* v. *Interlace Medical, Inc.*, Civil Action No. 10-10951-RWZ, U.S. District Court for the District of Massachusetts (14 pages).
Reexamination No. 95/001,933, Appendix 6 to Request for Inter Partes Reexamination of U.S. Pat. No. 7,226,459, Opening Markman Brief of Plaintiff Smith & Nephew, Inc. dated Oct. 13, 2010, in *Smith & Nephew, Inc.* v. *Interlace Medical, Inc.*, Civil Action No. 10-10951-RWZ, U.S. District Court for the District of Massachusetts (23 pages).
Reexamination No. 95/001,933, Appendix 7 to Request for Inter Partes Reexamination of U.S. Pat. No. 7,226,459, Defendant Interlace Medical, Inc's Responsive Markman Brief (Redacted) dated Oct. 27, 2010, in *Smith & Nephew, Inc.* v. *Interlace Medical, Inc.*, Civil Action No. 10-10951-RWZ, U.S. District Court for the District of Massachusetts (26 pages).
Reexamination No. 95/001,933, Appendix 8 to Request for Inter Partes Reexamination of U.S. Pat. No. 7,226,459, Plaintiff Smith & Nephew, Inc.'s Reply in Support of Markman Brief dated Nov. 3, 2010, in *Smith & Nephew, Inc.* v. *Interlace Medical, Inc.*, Civil Action No. 10-10951-RWZ, U.S. District Court for the District of Massachusetts (8 pages).
Reexamination No. 95/001,933, Examiner's Answer mailed Mar. 25, 2015 (3 pages).
Reexamination No. 95/001,933, Executed Expert Declaration of Hal Walbrink in support of Request for Inter Partes Reexamination of U.S. Pat. No. 7,226,459, Executed Mar. 9, 2012 (42 pages).
Reexamination No. 95/001,933, First Office Action mailed Jun. 5, 2012 (37 pages).
Reexamination No. 95/001,933, Litigation Search Report CRU 3999 dated Mar. 29, 2012 (24 pages).
Reexamination No. 95/001,933, Order Granting Request for Reexamination mailed Jun. 5, 2012 (29 pages).
Reexamination No. 95/001,933, Patent Owner's Apr. 14, 2014 Appeal Brief (334 pages).

(56) References Cited

OTHER PUBLICATIONS

Reexamination No. 95/001,933, Patent Owner's Feb. 13, 2014 Notice of Appeal (2 pages).
Reexamination No. 95/001,933, Patent Owner's Aug. 6, 2012 Response to First Office Action mailed Jun. 5, 2012 (156 pages).
Reexamination No. 95/001,933, Patent Owner's Jun. 3, 2013 Response to Second Office Action mailed Apr. 1, 2013 (37 pages).
Reexamination No. 95/001,933, Patent Owner's Oct. 21, 2013 Response to Action Closing Prosecution mailed Sep. 19, 2013 (180 pages).
Reexamination No. 95/001,933, Right of Appeal Notice mailed Jan. 14, 2014 (58 pages).
Reexamination No. 95/001,933, Second Office Action mailed Apr. 1, 2013 (56 pages).
Reexamination No. 95/001,933, Third Party's Dec. 19, 2012 Response to Notification of Defective Paper and Comments on First Office Action mailed Jun. 5, 2012 (38 pages).
Reexamination No. 95/001,933, Third Party's Jul. 3, 2013 Comments on Second Office Action mailed Apr. 1, 2013 (62 pages).
Reexamination No. 95/001,933, Third Party's Mar. 12, 2012 Request for Inter Partes Reexamination of U.S. Pat. No. 7,226,459 (130 pages).
Reexamination No. 95/001,933, Third Party's May 14, 2014 Respondent's Brief (303 pages).
Reexamination No. 95/001,933, Third Party's Nov. 20, 2013 Comments on Action Closing Prosecution mailed Sep. 19, 2013 (38 pages).
Reexamination No. 95/001,933, Third Party's Sep. 5, 2012 Comments on First Office Action mailed Jun. 5, 2012 (210 pages).
Reexamination No. 95/001,955, Appendix 19 to Request for Inter Partes Reexamination of U.S. Pat. No. 8,061,359, Opening Claim Construction Brief of Defendant Hologic, Inc., dated Feb. 24, 2012, in *Smith & Nephew, Inc.* v. *Hologic, Inc.*, Civil Action No. 11-12064-RWZ, U.S. District Court for the District of Massachusetts (24 pages).
Reexamination No. 95/001,955, Appendix 20 to Request for Inter Partes Reexamination of U.S. Pat. No. 8,061,359, Opening Markman Brief of Plaintiff Smith & Nephew, Inc., dated Feb. 24, 2012, in *Smith & Nephew, Inc.* v. *Hologic, Inc.*, Civil Action No. 11-12064-RWZ, U.S. District Court for the District of Massachusetts (24 pages).
Reexamination No. 95/001,955, Appendix 28 to Request for Inter Partes Reexamination of U.S. Pat. No. 8,061,359, Claim chart for anticipation of claims 1-8 based on U.S. Pat. No. 5,456,689 to Kresch (4 pages).
Reexamination No. 95/001,955, Appendix 29 to Request for Inter Partes Reexamination of U.S. Pat. No. 8,061,359, Claim chart for anticipation of claims 1-8 based on U.S. Pat. No. 6,032,673 to Savage (13 pages).
Reexamination No. 95/001,955, Appendix 30 to Request for Inter Partes Reexamination of U.S. Pat. No. 8,061,359, Claim chart for anticipation of claims 1-8 based on U.S. Pat. No. 3,945,375 to Banko (4 pages).
Reexamination No. 95/001,955, Decision Denying Petition mailed Sep. 28, 2012 (5 pages).
Reexamination No. 95/001,955, Executed Expert Declaration of Dr. Henry A. Dominicis in support of Request for Inter Partes Reexamination of U.S. Pat. No. 8,061,359, Executed Apr. 1, 2012 (150 pages).
Reexamination No. 95/001,955, Executed Expert Declaration of Hal Walbrink in support of Request for Inter Partes Reexamination of U.S. Pat. No. 8,061,359, Executed Apr. 2, 2012 (22 pages).
Reexamination No. 95/001,955, Litigation Search Report CRU 3999 dated Apr. 3, 2012 (33 pages).
Reexamination No. 95/001,955, Order Denying Request for Inter Partes Reexamination mailed Jun. 4, 2012 (35 pages).
Reexamination No. 95/001,955, Request for Inter Partes Reexamination of U.S. Pat. No. 8,061,359, filed Apr. 2, 2012 (265 pages).
Reexamination No. 95/001,955, Request for Reconsideration of Third Party Requestor's Petition for Reexamination mailed Jul. 3, 2012 (32 pages).
Reexamination No. 95/002,058, Executed Expert Declaration of Dr. Henry A. Dominicis in support of Request for Inter Partes Reexamination of U.S. Pat. No. 8,061,359, Executed Jul. 24, 2012 (101 pages).
Reexamination No. 95/002,058, First Action Closing Prosecution mailed Aug. 9, 2013 (34 pages).
Reexamination No. 95/002,058, First Office Action mailed Sep. 19, 2012 (37 pages).
Reexamination No. 95/002,058, Litigation Search Report CRU 3999 dated Aug. 13, 2012 (29 pages).
Reexamination No. 95/002,058, Patent Owner's Mar. 5, 2015 Notice of Appeal (2 pages).
Reexamination No. 95/002,058, Patent Owner's Jan. 22, 2013 Response to First Office Action mailed Sep. 19, 2012 (379 pages).
Reexamination No. 95/002,058, Patent Owner's Mar. 24, 2014 Response to Second Office Action mailed Jan. 24, 2014 (55 pages).
Reexamination No. 95/002,058, Patent Owner's Sep. 29, 2014 Response to Second Action Closing Prosecution mailed Aug. 27, 2014 (12 pages).
Reexamination No. 95/002,058, Patent Owner's Sep. 9, 2013 Response to First Action Closing Prosecution dated Aug. 9, 2013 (159 pages).
Reexamination No. 95/002,058, Reexam Order mailed Sep. 19, 2012 (54 pages).
Reexamination No. 95/002,058, Right of Appeal Notice mailed Feb. 4, 2015 (35 pages).
Reexamination No. 95/002,058, Second Action Closing Prosecution mailed Aug. 27, 2014 (35 pages).
Reexamination No. 95/002,058, Second Office Action mailed Jan. 24, 2014 (31 pages).
Reexamination No. 95/002,058, Third Party's Apr. 23, 2014 Comments on Second Office Action mailed Jan. 24, 2014 (117 pages).
Reexamination No. 95/002,058, Third Party's Feb. 21, 2013 Comments on First Office Action mailed on Sep. 19, 2012 (771 pages).
Reexamination No. 95/002,058, Third Party's Jul. 24, 2012 Request for Inter Partes Reexamination of U.S. Pat. No. 8,061,359 (1050 pages).
Reexamination No. 95/002,058, Third Party's Oct. 19, 2012 Request for Reconsideration of Certain Decisions Regarding Third Party Requestor's Request for Reexamination of U.S. Pat. No. 8,061,359 (19 pages).
Reexamination No. 95/002,058, Third Party's Oct. 29, 2014 Comments on Second Action Closing Prosecution mailed Aug. 27, 2014 (31 pages).
Reexamination No. 95/002,058, Third Party's Oct. 9, 2013 Comments on First Action Closing Prosecution mailed Aug. 9, 2013 (25 pages).
Reference AQ "Fishing Reel produced and sold by Shimano of Japan in to the U.S. prior to Oct. 26, 2001," as cited in the IDS filed Oct. 17, 2005 in the prosecution file history of U.S. Appl. No. 09/983,810 (7 pages).
Richard Wolf "'Morce—Power 2306' Electronic Morcellator" (2 pages).
Richard Wolf "The Fluid Manager" (2 pages).
Sheth, "Fiberoptic Light for Oophorectomy at Vaginal Hysterectomy", Journal of Gynecologic Surgery, vol. 14, No. 3, pp. 119-122, 1998 (4 pages).
Sugimoto "A Color Atlas of Hysteroscopy" Springer-Verlag Tokyo, 1999 (17 pages).
U.S. Appl. No. 09/486,977, Office Action mailed Sep. 7, 2005 (7 pages).
U.S. Appl. No. 11/780,759, Applicant's Mar. 31, 2011 Response to Office Action mailed Jan. 5, 2010 (15 pages).
U.S. Appl. No. 11/780,759, Applicant's Oct. 25, 2010 Response to Office Action mailed Jul. 26, 2010 (13 pages).
U.S. Appl. No. 11/780,759, Office Action mailed Jan. 5, 2011 (7 pages).
U.S. Appl. No. 11/780,759, Office Action mailed Jul. 22, 2010 (5 pages).
U.S. Appl. No. 11/780,759, Office Action mailed Jul. 26, 2010 (7 pages).
U.S. Appl. No. 11/929,938, Office Action mailed Jan. 5, 2011 (10 pages).

(56) References Cited

OTHER PUBLICATIONS

U.S. Appl. No. 11/929,938, Office Action mailed Jul. 30, 2010 (10 pages).
U.S. Appl. No. 11/929,940, Advisory Action mailed Sep. 10, 2010 (3 pages).
U.S. Appl. No. 11/929,940, Office Action mailed Dec. 30, 2009 (9 pages).
U.S. Appl. No. 11/929,940, Office Action mailed Jul. 1, 2010 (12 pages).
Valle "Hysteroscopic Removal of Submucous Leiomyomas", Journal of Gynecologic Surgery, vol. 6, No. 1, pp. 89-96, 1990 (9 pages).
Weck "A Direct Path to Diagnostic and Operative Control: The Weck-Baggish Hysteroscopy System" Advertisement, Journal of Gynecologic Surgery, vol. 7, No. 1, 1991 (2 pages).
Williamson et al., Editorial 1 "Complications of hysteroscopic treatments of menorrhagia", British Journal of Anesthesia, vol. 77, No. 3, pp. 305-308, 1996 (4 pages).
Reexamination No. 95/002,058, Patent Owner's May 5, 2015 Appeal Brief (47 pages).
Reexamination No. 95/002,058, Third Party's Jun. 5, 2015 Respondent Brief (21 pages).
Reexamination No. 95/002,058, Patent Owner's Jul. 1, 2015 Corrected Appeal Brief (47 pages).

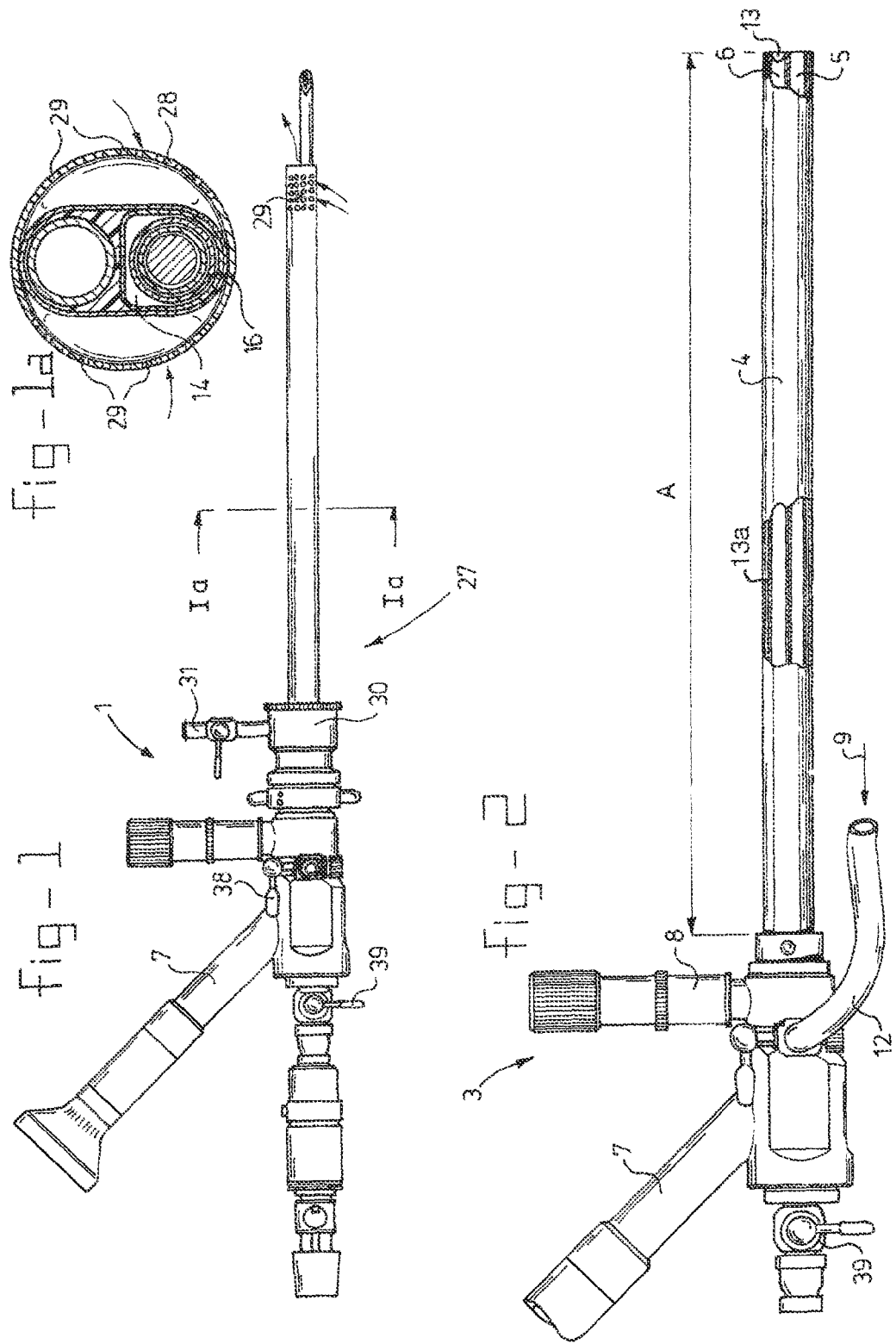

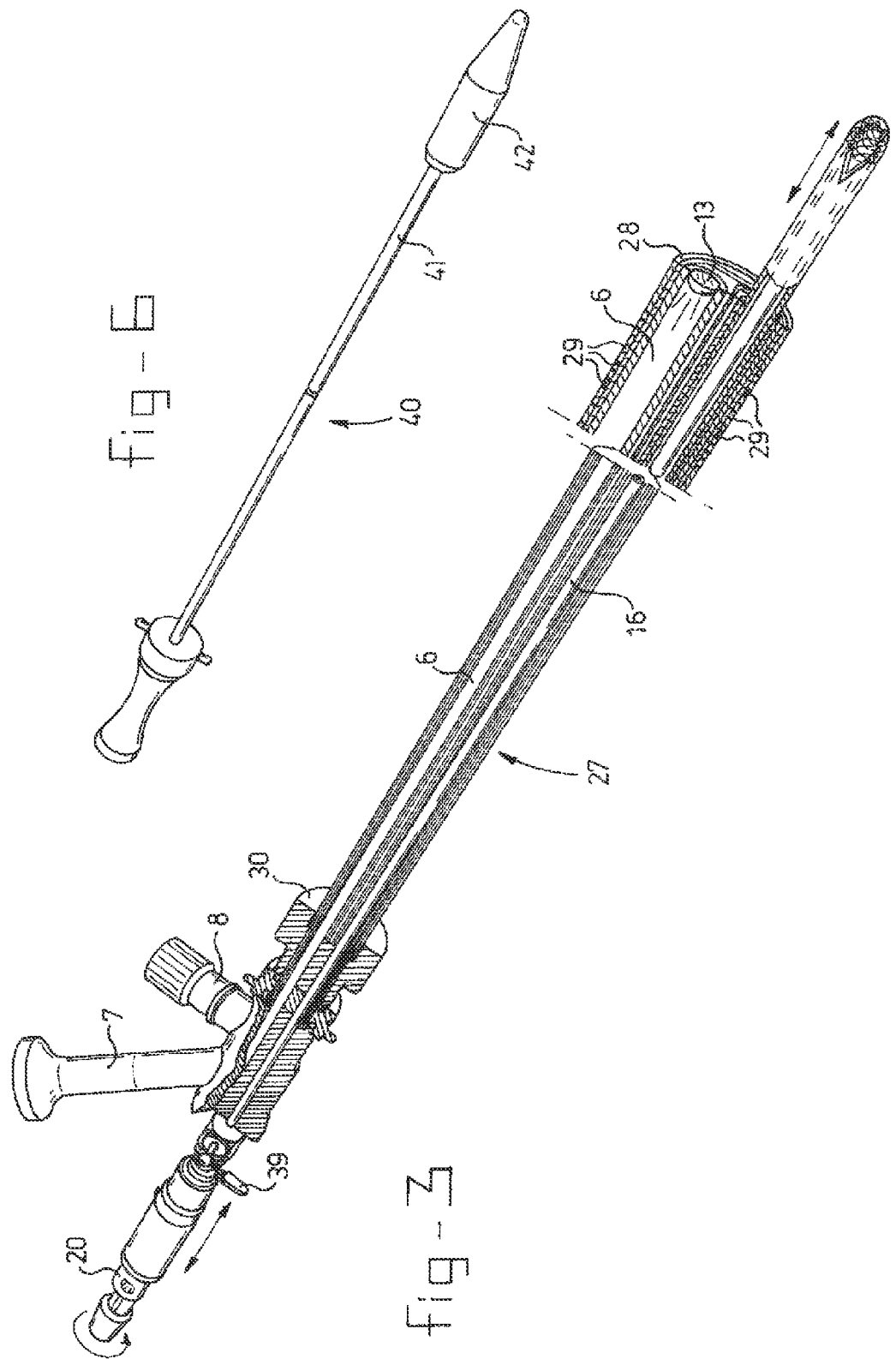

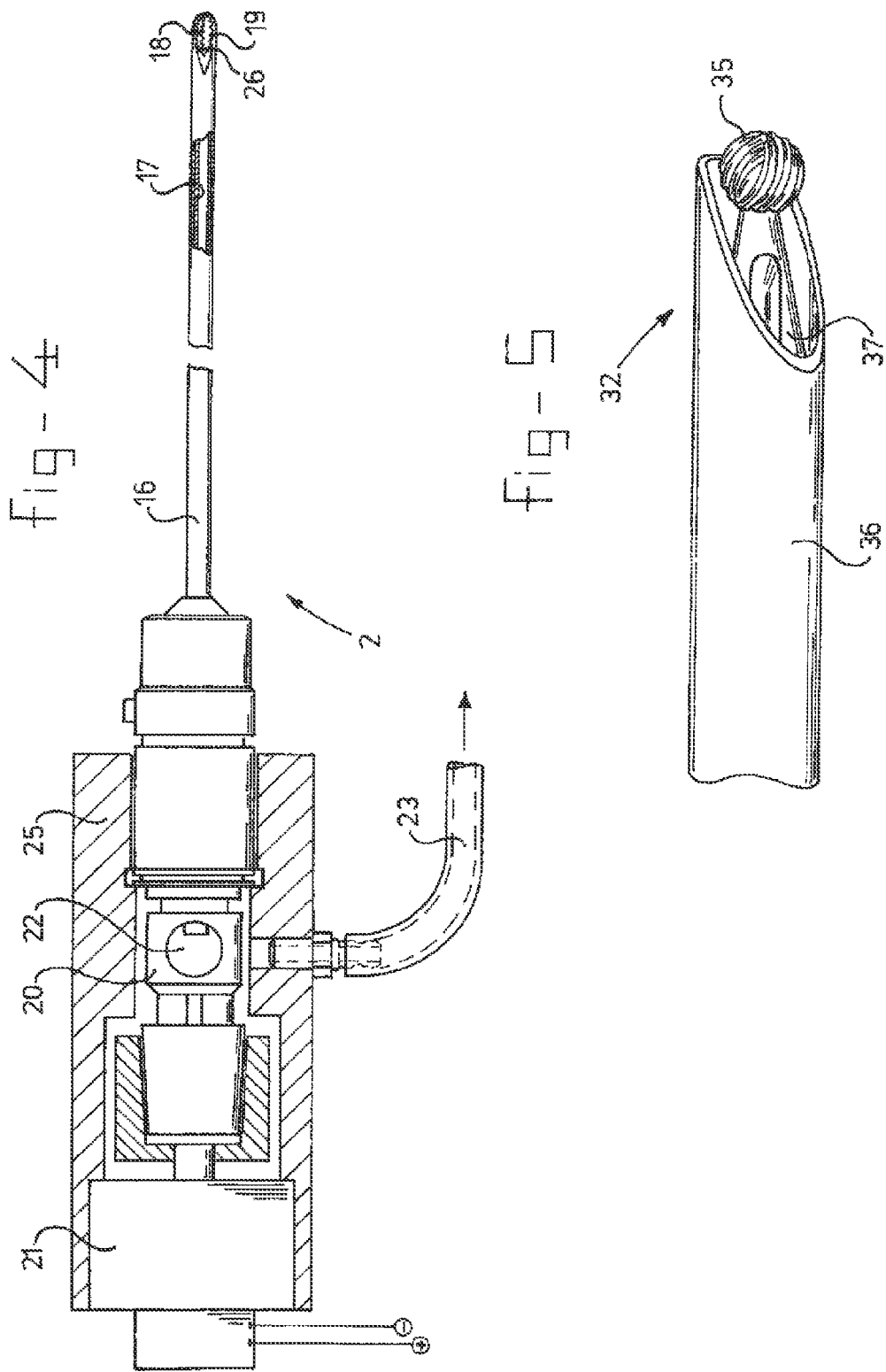

SURGICAL CUTTING DEVICE AND METHOD FOR ITS USE

CROSS-REFERENCE TO RELATED APPLICATIONS

This application is a continuation of prior application Ser. No. 14/081,801, filed on Nov. 15, 2013, now allowed, which is a continuation of prior application Ser. No. 11/929,940, filed on Oct. 30, 2007, now abandoned, which is a divisional of prior application Ser. No. 11/780,759, filed on Jul. 20, 2007, now U.S. Pat. No. 8,061,359, which is a continuation of application Ser. No. 09/486,977, filed on Mar. 6, 2000, now U.S. Pat. No. 7,249,602, which was the National Stage of International Application No. PCT/NL98/00504, filed Sep. 4, 1998, which claims the benefit of and priority to Netherlands Application No. 1006944, filed Sep. 4, 1997, each of the above applications is hereby incorporated by reference herein in its entirety.

FIELD OF THE INVENTION

The present invention relates to a surgical endoscopic cutting device.

BACKGROUND OF THE INVENTION

Surgical cutting devices are generally known and used for the removal of hard and/or soft tissue, such as in the vicinity of the knee joint. Such cutting devices are used in, for example, a joint cavity, where they can be guided endoscopically by separately inserting a viewing device having a light source and an observation portion. Such operations are successfully used in organs and joints lying not too deep underneath the skin.

When operations are being carried out on organs lying deeper, other techniques are currently used. If, for example, tissue has to be removed from the uterus, prostate, or urinary bladder, such as mucous membrane or other tissues, it was customary until now to use a so-called "loop." This is a loop-shaped cutting wire which is brought to a first potential, while the wall of the uterus is brought to a second, different potential. Tissue is removed by moving the loop along the uterus wall. In order to be able to carry out such an operation, it is necessary to dilate the uterus. Dilation is carried out by introducing a fluid. In order to maintain the effect of the potential difference, a non-conducting fluid is used, for example a 5% sorbitol solution. Because wounds are caused during the treatment described above, a good part of this fluid is resorbed into the patient's bloodstream (by way of the uterus). This can lead to highly dangerous electrolyte displacements. It has been found that the tissue can be removed more easily by working with a high-frequency monopolar electric current, but there is a risk of high-frequency electric current leading to internal and external burns. The loop is generally fitted on an endoscope and moved back and forth along the uterus wall with the endoscope. The tissue cut off during this treatment has to be removed from the uterus, which considerably extends the duration of the operation. Furthermore, the doctor has to check that all detached material actually has been removed.

This means that such operations are very time-consuming and require the surgeon to repeatedly move the device back and forth. This is tiring and consequently difficult to learn. Moreover, the patient has to be monitored continually during the operation, in order to prevent the undesirable phenomena described above. It is not uncommon for such an operation to be broken off because the patient's life is endangered by the side effects.

On the other hand, it is desirable to be able to carry out such operations instead of simply performing a hysterectomy.

WO 96/11638 discloses a cutter including a hollow stem and a cutting head accommodated inside a rigid housing. This rigid housing likewise contains a viewing channel with the necessary optics. U.S. Pat. No. 5,195,541 describes a laparoscopic discectomy apparatus. For a laparoscopic method it is essential to inflate the related cavity using gas. The gas feed is discontinuous and has no effect on viewing of the operation site.

Fluid is introduced by way of a space between the stem and the rigid housing and discharged together with the detached tissue through the hollow stem of the cutter.

This device could be satisfactory for the removal of tissues from certain body cavities, such as from the bladder. However, in the case of other body cavities, it is necessary to "blow up" the cavity before treatment can be carried out. An example of this is the uterus, in which it is important that the amount of enlargement of the organ be accurately controlled. The irregular discharge of fluid through the hollow stem of the cutter, caused partly by the irregular release of tissue, means that it cannot be guaranteed that the pressure inside the cavity is accurately controlled.

Such a device is consequently not very suitable for use in the treatment of such a cavity.

SUMMARY OF THE INVENTION

The object of the present invention is to provide a device which can perform such a treatment.

According to the invention, a further outlet channel is provided, the function of which is independent of whether or not detached tissue has been released. In other words, a regular discharge of fluid can occur through this further outlet channel. Since only a minor part of the fluid is now discharged through the outlet, in which there are detached pieces of tissue, the pressure inside the body cavity can be regulated and controlled accurately. This makes it possible to remove undesired tissue from cavities such as the uterus. The applicability of the removal of tissues by cutting is consequently considerably increased.

The further outlet channel described above is formed by an insertion tube fitted around the endoscopic device. This insertion tube serves to clear a space for the endoscopic device. For this purpose, the front side of the insertion tube can be provided with an insertion mandrel, which is removed after the positioning of the insertion tube and replaced by the endoscopic device described above. In this case the further outlet channel can be defined between the endoscopic device and the insertion tube.

In the case of such a construction it is desirable for a coupler to be present to provide a coupling between the rigid housing and the insertion tube described above.

Discharge of the tissue material which has been detached can be achieved either by making the stem on which the cutting elements are fitted hollow, or by fitting a protective tube around the cutter. Such a protective tube can also be used without the space between protective tube and stem serving as an outlet channel. This means that the cutter can be designed as a separate unit which can be coupled to the rigid housing, which has advantages in particular for purposes of sterilization. Namely, the device can then be detached in a simple way.

For the removal of tissue from a uterus it is essential for the rigid housing to have a length which is sufficient to reach all tissue parts, i.e. a length of at least 30 cm.

The observation part of the device described above includes a light channel in the housing, provided near one end with a lens and near the other end with an observation mechanism. The latter can include an eyepiece or a connection for a camera so that the surgeon can carry out the operation using a monitor and others can possibly look at the same time.

The cutting elements described above can include any cutting element known in the prior art. In other words, a cutting head with cutting faces can be used, but it is also possible to use constructions with teeth, meshing with the protective tube or otherwise. In the latter instance, the protective tube is preferably provided with a lateral opening through which a part of the cutting elements extends so that on each revolution, part of the tissue is removed and can be discharged directly through the interior of the drive/discharge tube of the cutter.

The invention also relates to a method for the removal of uterus tissue in which the device described above is used. In other words, a machining operation is now applied with the use of a physiological fluid which can be electrically conducting without any problem, while at the same time the removed tissue is sucked out. It is, of course, possible to suck out the tissue at a later stage. The machining operation is carried out by a rotating action.

According to a further embodiment of the method, an outlet and a further outlet are present, and the pressure inside the body cavity is regulated by metering the quantity of fluid which moves through the further outlet. The insertion of the surgical endoscopic cutting device is preferably carried out in the manner described above using an insertion mandrel and insertion tube.

BRIEF DESCRIPTION OF DRAWINGS

The invention will be explained in greater detail below with reference to an exemplary embodiment shown in the drawings, in which:

FIG. 1 shows the endoscopic cutting device according to the invention in the assembled state, in side view and partially in section;

FIG. 1a shows the viewing/receiving part of the cutting device of FIG. 1 in section along the line Ia-Ia;

FIG. 2 shows a side and partially cut-away view of the viewing/receiving part of the cutting device of FIG. 1;

FIG. 3 shows a partially cut-away perspective view of the device of FIG. 1, with the insertion end enlarged;

FIG. 4 shows a partially sectional side view of the cutter of the cutting device of FIG. 3;

FIG. 5 shows a variant of the cutter shown in FIG. 4; and

FIG. 6 shows an insertion mandrel according to the invention.

DETAILED DESCRIPTION

The endoscopic cutting device according to the invention is indicated in its entirety by 1 in FIG. 1. It comprises a viewing/receiving part 3, which is shown in FIG. 2, a cutting part 2, which is shown in greater detail in FIGS. 4 and 5, and an insertion mandrel, which is shown in FIG. 6.

With reference to FIG. 2, it can be seen that the viewing/receiving part 3, is composed of an outer tube 4 in which a main channel 5 and viewing channel 6 are defined. Viewing channel 6 ends at one side in a lens 13 and at the other side in a viewing tube 7, on which an eyepiece or camera connection is placed. A connection 8 for a light source is also present, for connection to a light guide, such as a fibre optics bundle 13a, which provides for lighting at the end of lens 13. Near the control end, tube 4 is provided with a fluid inlet 9 connected to a hose 12, for adding a physiological salt solution.

A shut-off valve is indicated by 39.

The length of the actual outer tube 4, is indicated by A and is more than 30 cm.

FIG. 4 shows details of the cutter or the cutting part 2, which is composed of a protective tube 16 inside of which a drive/suction tube 17 is fitted. Near the working end, tube 17 is provided with teeth 19 which mesh with teeth 18 provided in an opening 26 in the end part of protective tube 16. Near the other end, drive/suction tube 17 is provided with a coupling 20, which can be connected at one end to a rotating drive motor 21, not shown in detail, and at the other end is provided with an opening 22 through which fluid and removed material can be discharged by way of suction tube 17 to the discharge hose 23. A pressure regulator can be present in this discharge hose 23, which is connected to a vacuum source.

In FIG. 1 the insertion part is indicated by 27. This insertion part is composed of an insertion tube 28 which is provided with openings 29 at one end and near the other end, the insertion part 27 is provided with a bayonet connection 30 and an outlet 31. Insertion tube 28 is designed in such a way that tube 4 can be fitted therein, as shown in FIGS. 1 and 3, while it is also possible to fit insertion mandrel 40, provided with stem 41 and mandrel 42, in insertion tube 28.

The construction described above has an inlet 38 for fluid. Inlet 38 extends to channel 14 (FIG. 1a), i.e. the space bounded between the outer tube 4 and the protective tube 16 and 36, respectively from FIG. 4 or 5. A shut-off valve 39, which is connected to channel 14, is present, while the further outlet is indicated by 31. A discharge hose 23 for tissue and fluid is shown. During the removal of tissue, with a substantially continuous supply of fluid through inlet 38, some of the fluid will be discharged through outlet 23. This relatively small amount will be mixed with a mixture released during the cutting operation. Most of the fluid will be discharged through the further outlet 31. This discharge is unimpeded and occurs through openings 29. Pressure variations occurring due to the presence or absence of removed tissue in channel 17 (FIG. 4) have little or no influence on the pressure inside the body cavity owing to the presence of the further outlet 31.

If the device is to be inserted into, for example, a uterus, insertion mandrel 40 will first be inserted, with shut-off valve 39 open, into insertion tube 28 with bayonet 30. This assembly is then placed in the uterus in a relatively simple manner due to the shape of mandrel 42. Mandrel 42 is then removed by manipulating stem 41, and the construction shown in FIG. 2 is placed in tube 28. Connection is made here to bayonet 30. The cutting action can then begin after the uterus has been dilated by the introduction of fluid. This fluid can be a physiological flushing and distension fluid, such as a physiological salt solution (NaCl 0.9%). In the event of the (unavoidable) resorption of the physiological fluid into the blood, electrolyte displacement, with fatal consequences for the patient, will not occur. Owing to the absence of electrical current, the burns described above are also ruled out.

By switching on motor 21, tube 17 is set in rotation and teeth 19 move regularly along cutting edge 18 of protective tube 16 which remains stationary. While they are moving along each other and picking up tissue material between them, a cutting, detaching action on the tissue material is occurring. The cut, detached material is removed through the interior of tube 17 and outlet 23.

The appropriate area of the uterus can be treated by moving parts 18 and 19 along the uterus wall or along tissue to be removed, which can be observed through viewing tube 7 by supplying light through connection 8.

Through the use of a continuous flow system, a constantly clear view is obtained for the observer even if blood and/or mucous is/are in the mixture. Moreover, the pressure can be maintained as low as possible, in order to prevent intravasation.

FIG. 5 shows a variant of the end of the cutter. The cutter or cutting part are indicated in their entirety by 32. The protective tube is indicated by 36 and is beveled near the end. The drive/suction tube is indicated by 37 and provided with a cutting head near the end. In this embodiment, there is either no interaction between cutting head 35 and protective tube 36, or head 35 and tube 36 interact near the edge of tube 36, which is adapted for that purpose by grinding.

It is understood that such cutting elements can be designed in any way known in the prior art.

These and further modifications are considered to lie within the scope of the present application, to be immediately obvious to the person skilled in the art after reading the description, and to lie within the scope of the appended claims. For instance, it is possible to effect the supply of working fluid and the discharge of cleaning material in another way, i.e., to arrange the interior of housing 4 slightly differently. Furthermore, the method described above can be used for the removal of other tissue material, such as prostate tissue through the urethra, or for the removal of tissue from the wall of the urinary bladder.

What is claimed is:

1. A method for removal of fibroid tissue from a uterus, comprising:
    transcervically inserting first and second discrete channels into the uterus, the first discrete channel having a first end in communication with an inlet valve such that a physiological salt solution is able to flow from the inlet valve into and through the first discrete channel and out of a second opposing end of the first discrete channel into the uterus, and the second discrete channel having an observation mechanism at a first end thereof and a lens adjacent to a second opposing end thereof, the second discrete channel being sealed from the first discrete channel to prevent the physiological salt solution from the inlet valve from entering the uterus through the second discrete channel;
    after the transcervically inserting of the first and the second discrete channels into the uterus, delivering the physiological salt solution into the uterus through the first discrete channel to distend the uterus;
    inserting a motor driven cutter into the first discrete channel such that a cutting region of the motor driven cutter extends past the second opposing end of the first discrete channel into the uterus, the motor driven cutter including an outer tube defining a cutting window and an inner tube received within the outer tube, the inner tube defining a lumen;
    energizing an electric motor;
    after the delivering the physiological salt solution into the uterus, cutting and detaching the fibroid tissue from the uterus using the energized motor driven cutter; and
    aspirating the cut and detached fibroid tissue and at least a portion of the a physiological salt solution from the uterus through the lumen of the inner tube of the motor driven cutter.

2. The method of claim 1, wherein the transcervically inserting the first and second discrete channels occurs prior to the inserting the motor driven cutter.

3. The method of claim 2, wherein the delivering the physiological salt solution occurs prior to the energizing the electric motor.

4. The method of claim 1, wherein the second discrete channel is a light channel.

5. The method of claim 4, further comprising coupling a light source to the light channel to provide light at the lens.

6. The method of claim 1, wherein the energizing causes the inner tube to rotate relative to the outer tube to cut and detach the fibroid tissue.

7. The method of claim 6, wherein the inner tube has a cutting element at a distal region thereof that cuts and detaches the fibroid tissue at the cutting window.

8. The method of claim 7, wherein the cutting element includes teeth.

9. The method of claim 1, wherein the transcervically inserting the first and second discrete channels into the uterus includes (i) transcervically inserting an insertion tube coupled with an insertion mandrel into the uterus, (ii) removing the insertion mandrel from the insertion tube, and (iii) inserting the first and second discrete channels into the insertion tube.

10. A method for removal of fibroid tissue from a uterus, comprising:
    transcervically inserting first and second discrete channels into the uterus, the first discrete channel having a straight, central longitudinal axis extending from a port to an opening at a distal tip of the first discrete channel, the port for receiving a motor driven cutter therethrough, and the second discrete channel having an observation mechanism at a proximal end thereof and a lens adjacent to a distal end thereof;
    after the transcervically inserting of the first and the second discrete channels into the uterus, introducing a physiological salt solution into the uterus;
    inserting the motor driven cutter into the first discrete channel through the port, the motor driven cutter including an outer tube defining a cutting window and an inner tube received within the outer tube, the inner tube defining a lumen;
    after the delivering the physiological salt solution into the uterus, cutting and detaching the fibroid tissue from the uterus using the motor driven cutter; and
    aspirating at least a portion of the a physiological salt solution with the cut and detached fibroid tissue from the uterus through the lumen of the inner tube of the motor driven cutter.

11. The method of claim 10, wherein the second discrete channel is a light channel.

12. The method of claim 11, further comprising coupling a light source to the light channel to provide light at the lens.

13. The method of claim 10, wherein the cutting and detaching the fibroid tissue includes rotating the inner tube relative to the outer tube.

14. The method of claim 13, wherein the inner tube has a cutting element at a distal region thereof that cuts and detaches the tissue at the cutting window.

15. The method of claim 14, wherein the cutting element includes teeth.

16. The method of claim 10, wherein the transcervically inserting the first and second discrete channels into the uterus includes (i) transcervically inserting an insertion tube coupled with an insertion mandrel into the uterus, (ii) removing the insertion mandrel from the insertion tube, and (iii) inserting the first and second discrete channels into the insertion tube.

17. The method of claim 10, wherein the transcervically inserting the first and second discrete channels occurs prior to the inserting the motor driven cutter.

18. The method of claim 10, wherein the second discrete channel is sealed from the first discrete channel to prevent the physiological salt solution from entering the uterus through the second discrete channel.

19. The method of claim 10, wherein the introducing the physiological salt solution into the uterus distends the uterus.

* * * * *